US012606592B2

(12) United States Patent
Wagh et al.

(10) Patent No.: US 12,606,592 B2
(45) Date of Patent: Apr. 21, 2026

(54) TRIPLE G-C-T BASE CODED NUCLEOBASE AMINO ACID, ITS SYNTHESIS AND PEPTIDE FORMATION

(71) Applicant: COUNCIL OF SCIENTIFIC AND INDUSTRIAL RESEARCH, New Delhi (IN)

(72) Inventors: Mahendra Ashok Wagh, Pune (IN); Gangadhar Jessy Sanjayan, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 329 days.

(21) Appl. No.: 17/961,220

(22) Filed: Oct. 6, 2022

(65) Prior Publication Data

US 2024/0083937 A1 Mar. 14, 2024

(51) Int. Cl.
*C07K 1/02* (2006.01)
*C07K 1/06* (2006.01)

(52) U.S. Cl.
CPC . *C07K 1/02* (2013.01); *C07K 1/06* (2013.01)

(58) Field of Classification Search
None
See application file for complete search history.

(56) References Cited

U.S. PATENT DOCUMENTS

2005/0009041 A1 1/2005 Buchardt et al.

OTHER PUBLICATIONS

Wagh et al. Three in one: Triple G-C-T base-coded brahma nucleobase amino acid: Synthesis, peptide formation, and structural features. Journal of Organic Chemistry (2021), 86(21), 15689-15694.*

Staatz. Synthesis of chiral liposome building blocks with s-triazine as linking unit. Liebigs Annalen der Chemie (1989), (1), 51-57.*

Talukder, et al., "Synthesis of alanyl nucleobase amino acids and their incorporation into proteins", Bioorg. Med. Chem., vol. 24, No. 18, pp. 4177-4187, Sep. 15, 2016.

Brodyagin, et al., "Chemical approaches to discover the full potential of peptide nucleic acids in biomedical applications", Beilstein Journal of Organic Chemistry, vol. 17, pp. 1641-1688.

Meena, et al., "Triazine-Based Janus G—C Nucleobase as a Building Block for Self-Assembly, Peptide Nucleic Acids, and Smart Polymers", The Journal of Organic Chemistry, vol. 86, pp. 3186-3195, 2021.

* cited by examiner

*Primary Examiner* — Maury A Audet

(74) *Attorney, Agent, or Firm* — DINSMORE & SHOHL LLP

(57) ABSTRACT

Triple G-C-T base coded nucleobase amino acids according to Formula (I):

(I)

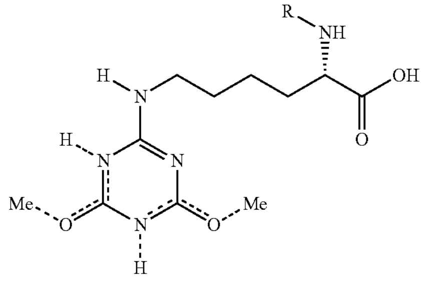

wherein R is —H or -Boc, are provided as building blocks for peptide sequences. The compound of formula (I) includes three recognition sites, DDA (G mimic), DAA (C mimic) and ADA (T mimic) that can simultaneously interact with two sets of nucleobases (C-A or G-A), at any given time. A one-step synthetic process for the triple G-C-T base coded nucleobase amino acids is provided.

10 Claims, 3 Drawing Sheets

9

9'

20 20' 20:20'

Scheme 3: Synthesis of fully deprotected peptide analogues (15) and (19)

11

12 (85%)

13 (quant.)

14 (82%)

15 (quant.)

16 (89%)

17 (quant.)

18 (86%)

19 (quant.)

TRIPLE G-C-T BASE CODED NUCLEOBASE AMINO ACID, ITS SYNTHESIS AND PEPTIDE FORMATION

CROSS-REFERENCES TO RELATED APPLICATIONS

This application claims benefit of priority under 35 U.S.C. § 119(a)-(d) to Indian Patent Application No. 202211047552, filed Aug. 18, 2022, which is incorporated by reference herein in its entirety.

TECHNICAL FIELD

The present invention relates to a triple G-C-T base coded nucleobase amino acid, process for the preparation and application in peptide formation thereof. More particularly, the present invention relates to a triple G-C-T base coded nucleobase amino acid of Formula (I) as building blocks for peptide sequences and its one step synthetic process thereof.

BACKGROUND

Nucleobase amino acids (NBA), as a distinctive class of unnatural amino acids have ushered into prominence primarily owing to their utility in nucleic acid recognition and nucleic acid-protein interaction studies. These amino acids, typically bearing synthetic or native nucleobases on the side chain of α-amino acid residues, are being increasingly employed for designing of polypeptides and proteins to interact with their nucleic acid substrates using Watson-Crick and other base pairing interactions.

Several Nucleobase amino acids have been reported recently; among them the prominent ones are alanyl-based NBAs (1-4 shown below) synthesized from serine lactone following multi-step synthetic routes. The homologs of alanyl NBA such as homoalanyl 5, 6 and norvalyl 7, 8 NBAs also have been explored for their utility in studying nucleic acid-protein recognitions.

1

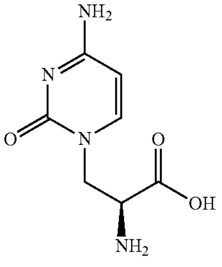

2

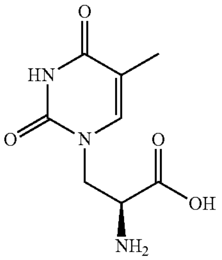

-continued

3

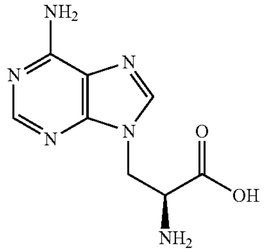

4

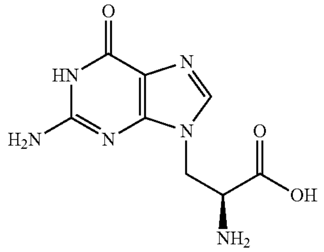

5

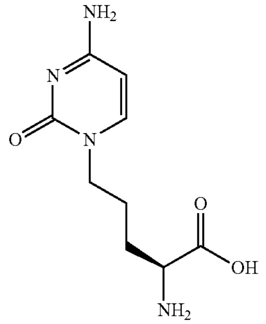

6

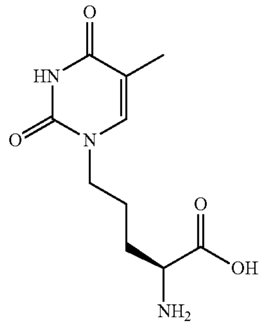

7

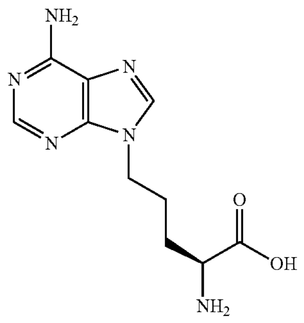

-continued

8

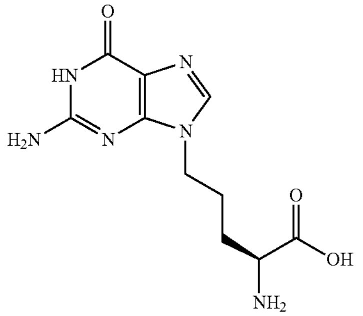

Recently, efforts are being made to develop NBA-based polypeptides and peptide nucleic acids (PNAs) containing double-sided Janus bases, which can code for two nucleobases simultaneously which are thus capable of bifacial recognition. The twin binding faces of Janus nucleobases facilitate their binding to both of the complementary strands of target RNA or DNA with stronger affinity.

SUMMARY

With a need for further development, the present inventors pursued their research to provide a triple G-C-T nucleobase amino acid (G-C-$T_{NBA}$), featuring three recognition sites that can simultaneously interact with two sets of nucleobases (C-A or G-A), at any given time.

A main objective of the present disclosure is to provide a triple G-C-T base coded nucleobase amino acid.

Another objective of the present disclosure is to provide a one-step synthetic process for the preparation of a triple G-C-T base coded nucleobase amino acid.

Yet another objective of the present disclosure is to provide an application of a triple G-C-T base coded nucleobase amino acid in the formation of peptide sequences.

Accordingly, to accomplish the objectives, the present disclosure provides a triple G-C-T base coded nucleobase amino acid of Formula (I):

(I)

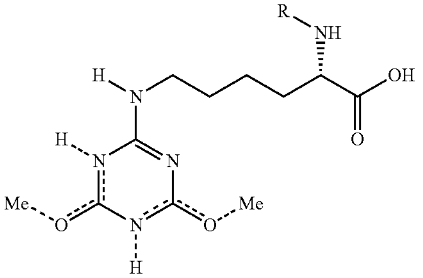

In formula (I), R is H or -Boc. The compound of formula (I) includes three recognition sites, DDA (G mimic), DAA (C mimic) and ADA (T mimic) that can simultaneously interact with two sets of nucleobases (C-A or G-A), at any given time.

In embodiments, a triple G-C-T base coded nucleobase amino acid of Formula (9) is provided, wherein the free triple G-C-T amino acid of Formula (9) can exist in the form (9') owing to the prototropy effect leading to "G-C" inversion. The compound of formula (9) displays the G and T faces and the compound of Formula (9') display C and T faces as shown in FIG. 1 suggesting that it can simultaneously interact with two sets of nucleobases (C-A or G-A), at any given time.

The triple G-C-T (guanine-cytosine-thymine) nucleobase amino acid (NBA) includes three recognition faces, DDA (G mimic), DAA (C mimic) and ADA (T mimic), that are complementary to native nucleobases cytosine (C), guanine (G), and adenine (A), respectively.

Another embodiment provides a one-step synthetic process for the preparation of free triple G-C-T amino acid of Formula (9). The process includes:

(a) reacting 2-chloro-4,6-dimethoxy-1,3,5-triazine (10) with α-Boc lysine in the presence of base and solvent at a temperature in the range of 35-40° C. for 1 hour to 2 hours to obtain Boc-protected G-C-T-amino acid intermediate (11); and (b) deprotecting Boc-group and demethylating intermediate (11) by using HBr/AcOH at a temperature from 35° C. to 40° C. for 1 hour to obtain free G-C-T amino acid of formula (9) in quantitative yield.

In embodiments, a single step process is provided for synthesis of the Boc-protected G-C-T-amino acid (11) key intermediate:

(11)

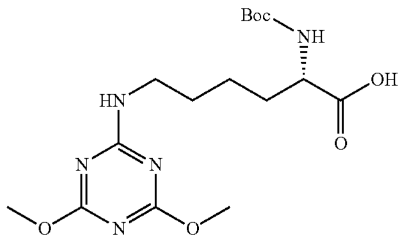

The process includes reacting 2-chloro-4,6-dimethoxy-1,3,5-triazine (10) with α-Boc lysine in the presence of base and solvent.

The Boc-protected G-C-T-amino acid (11) acts as a key intermediate to introduce the G-C-T NBA building block into peptides sequences from both the N-terminus and the C-terminus.

Yet another embodiment provides a process for the synthesis of peptide sequences/assembly at the backbone of nucleobase, wherein said process comprises:

(i) coupling the C-termini of Boc-protected G-C-T-amino acid (11) with alpha-amino acid to obtain the peptides;

(ii) deprotecting the Boc group to obtain free peptide amine;

(iii) Coupling the free peptide amine at N-terminus further with Boc-protected alpha amino acid to obtain the Boc-protected peptide sequence followed by concurrent saponification, deprotection and O-demethylation to obtain the desired peptide sequence.

Due to availability of both C and N termini for further modifications, the triple G-C-T nucleobase amino acid (9) and (11) finds wide-ranging application for nucleic acid recognition and nucleic acid-peptide/protein interaction studies.

Acronyms used herein:

HBr: Hydrobromic acid

AcOH: Acetic acid

HBTU: Hexafluorophosphate Benzotriazole Tetramethyl Uronium

HOAt: 1-Hydroxy-7-azabenzotriazole

TFA: Trifluoroacetic acid

DCM: Dichloromethane

DETAILED DESCRIPTION

The invention now will be described in detail in connection with certain preferred and optional embodiments, so that various aspects thereof may be more fully understood and appreciated.

Embodiments herein provide a triple G-C-T base coded nucleobase amino acid of Formula (I):

(I)

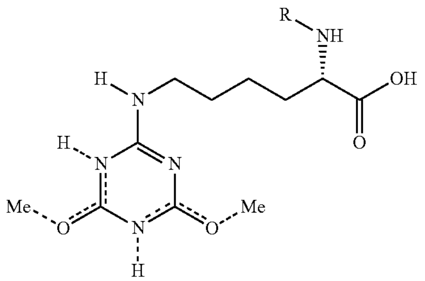

wherein, R=H or -Boc.

The compound of formula (I) includes three recognition sites, DDA (G mimic), DAA (C mimic) and ADA (T mimic) that can simultaneously interact with two sets of nucleobases (C-A or G-A), at any given time.

It should be understood that formula (I) encompasses compounds of formula (Ia) and compounds of formula (Ib):

(Ia)

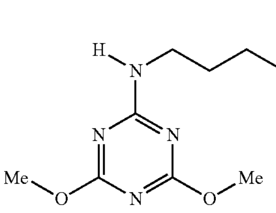

-continued (Ib)

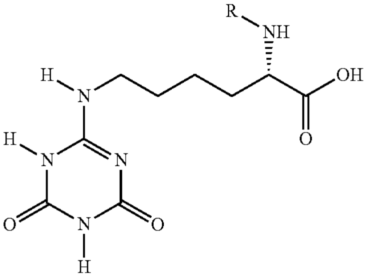

In formula (Ia) and formula (Ib), R is H or -Boc.

In embodiments, a triple G-C-T base coded nucleobase amino acid of Formula (9) is provided, wherein the free triple G-C-T amino acid of Formula (9) can exist in the form (9') owing to the prototropy effect leading to "G-C" inversion.

(9)

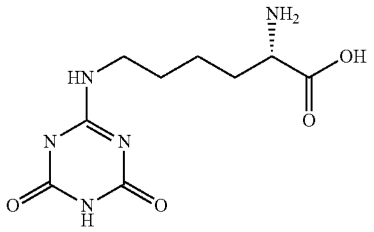

(9')

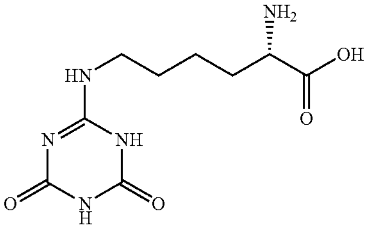

Figure 1:
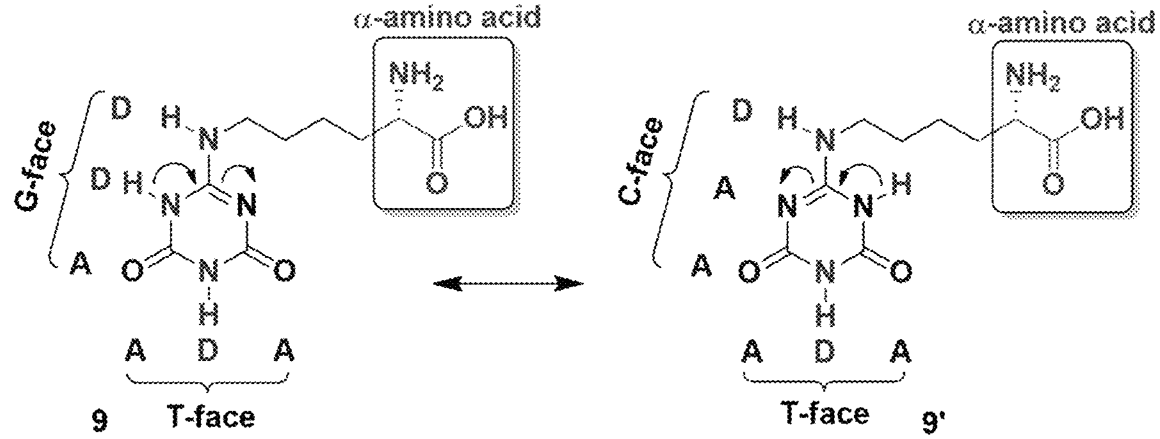
FIG. 1: Depicts Triple G-C-T base coded nucleobase amino acid NBA 9 displaying G and T bases and tautomerism leading to "G-C" inversion to form 9' displaying C and T bases.
Figure 2A:
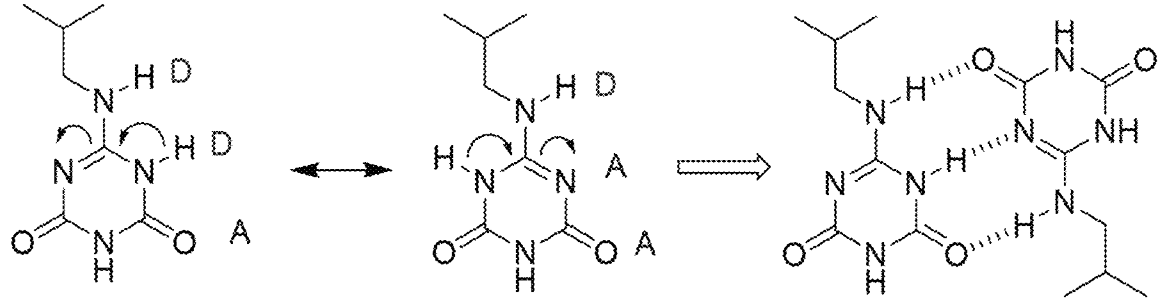
FIG. 2A depicts a molecular structure of the model compound 20 (left), its tautomerized form 20' (center), and duplex formation 20:20' (right) owing to G-C canonical Watson-Crick-type hydrogen-bonding, confirming that the present compound could exist in both G (20) and C (20') forms.
Figure 2B:
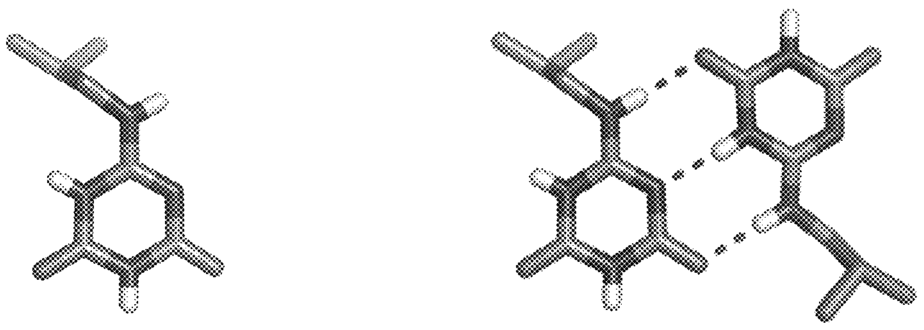
FIG. 2B depicts a crystal structure of a model compound 20 (left) and its dimer showing G-C-type hydrogen bonding (right).

As illustrated in FIG. 1, the compound of formula (9) displays the G and T faces, and the compound of Formula (9') displays C and T faces, suggesting that it can simultaneously interact with two sets of nucleobases (C-A or G-A), at any given time.

The triple G-C-T (guanine-cytosine-thymine) nucleobase amino acid (NBA) of Formula (9) includes three recognition faces, DDA (G mimic), DAA (C mimic), and ADA (T mimic), that are complementary to native nucleobases cytosine (C), guanine (G), and adenine (A), respectively.

Further embodiments herein provide a one-step synthetic process for the preparation of free triple G-C-T amino acid of Formula (9). The process includes:

(a) reacting 2-chloro-4,6-dimethoxy-1,3,5-triazine (10) with α-Boc lysine in the presence of base and solvent at a temperature from 35° C. to 40° C. for 1 hour to 2 hours to obtain Boc-protected G-C-T-amino acid intermediate (11); and (b) deprotecting Boc-group and demethylating intermediate (11) by using HBr/AcOH at a temperature from 35° C. to 40° C. for 1 hour to obtain free G-C-T amino acid of formula (9) in quantitative yield.

The base for the reaction is selected from organic bases such as N,N-diisopropylethylamine (DIPEA) and triethylamine ($Et_3N$). In a particularly useful embodiment, base is N,N-diisopropylethylamine (DIPEA).

The solvent comprises polar protic solvent such as methanol and ethanol. In particularly useful embodiment, solvent is dry methanol.

The process is carried out at ambient temperature, such as from 35° C. to 40° C.

Another embodiment of the present invention provides a Boc-protected triple G-C-T nucleobase amino acid of the Formula (11) as a building block for peptide sequences:

(11)

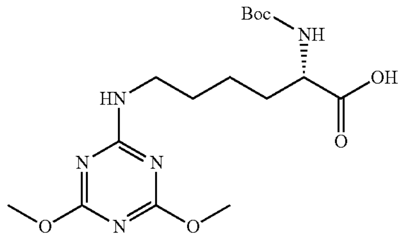

The Boc-protected triple G-C-T nucleobase amino acid of the Formula (11) includes three recognition sites, DDA (G mimic), DAA (C mimic), and ADA (T mimic), that can simultaneously interact with two sets of nucleobases (C-A or G-A), at any given time.

In embodiments, a single step process is provided for the synthesis of the Boc-protected G-C-T-amino acid (11), a key intermediate, wherein said process comprises of reacting 2-chloro-4,6-dimethoxy-1,3,5-triazine (10) with α-Boc lysine in the presence of base and solvent as depicted below in Scheme 1.

Scheme 1

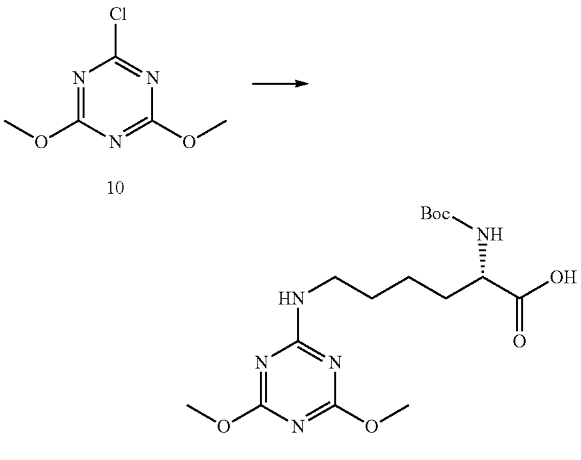

10

11 (72%)

The Boc-protected G-C-T-amino acid (11) acts as a key intermediate to introduce the G-C-T NBA building block into peptides sequences from both the N-terminus and the C-terminus.

The compound (11) is synthesized in multi-gram scale in one step using cheap and commercially available 2-chloro-4,6-dimethoxy-1,3,5-triazine (10). The compound (10) is readily prepared in large amounts starting from cyanuric chloride by a process known in the art, such as the processes disclosed in *J. Org. Chem.,* 2018, 83, 10916-10921 and *J. Org. Chem.,* 2019, 84, 5893-5898.

The base for the reaction is selected from organic bases such as N,N-diisopropylethylamine (DIPEA) and triethylamine ($Et_3N$). In a particularly useful embodiment, the base is N,N-diisopropylethylamine (DIPEA).

The solvent comprises a polar protic solvent such as methanol and ethanol. In a particularly useful embodiment, solvent is dry methanol.

The process is carried out at ambient temperature, such as from 35° C. to 40° C.

The Boc-protected G-C-T-amino acid of Formula (11) acts as a key NBA building block intermediate, which can be incorporated into peptide sequences from both N-terminus and C-terminus.

Yet another embodiment provides a general process for the synthesis of peptide assembly from Boc-protected G-C-T-amino acid of Formula (11). The process includes:

(i) coupling the C-termini of Boc-protected G-C-T-amino acid (11) with alpha-amino acid in the presence of HBTU/HOAt in DMF at a temperature from 0° C. to 40° C. for 17 hours to 18 hours to obtain the peptides;

(ii) deprotecting the Boc group at a temperature from 0° C. to 40° C. for 30 minutes to 40 minutes by using a TFA:DCM (1:1) mixture to obtain free peptide amine;

(iii) coupling the free peptide amine at the N-terminus further with Boc-protected alpha amino acid in the presence of HBTU/HOAt in DMF at a temperature from 0° C. to 40° C. for 17 hours to 18 hours to obtain the Boc-protected peptide sequence followed by concurrent saponification, deprotection and O-demethylation, to obtain the desired peptide sequence.

In embodiments, a process is provided for the preparation of a tripeptide (15) from Boc-protected G-C-T-amino acid of Formula (11) The process includes:

(i) coupling the C-termini of Boc-protected G-C-T-amino acid (11) with $NH_2$-Phe-OMe in the presence of HBTU/HOAt in DMF at a temperature from 0° C. to 40° C. for a period of 17 hours to 18 hours to afford the dipeptide (12);

(ii) deprotecting selectively Boc group of dipeptide (12) at a temperature from 0° C. to 40° C. by using TFA:DCM (1:1) mixture for 30 to 40 minutes to obtain free peptide amine (13);

(iii) coupling the free peptide amine (13) at the N-end with Boc-Ala-OH in the presence of HBTU/HOAt in DMF at a temperature from 0° C. to 40° C. to afford the Boc-protected tripeptide (14); and (iv) subjecting the Boc-protected tripeptide (14) to ester saponification at a temperature from 0° C. to 40° C. in water for 4 hours, followed by concurrent Boc-deprotection and O-demethylation by using HBr in AcOH at a temperature from 35° C. to 40° C. for 1 hour to afford deprotected tripeptide (15).

In embodiments, a process is provided for preparing pentapeptide (19) from Boc-protected G-C-T-amino acid of Formula (11). The process comprises:

(i) coupling the C-termini of Boc-protected G-C-T-amino acid (11) with $NH_2$-Val-Phe-OMe in the presence of HBTU/HOAt in DMF at a temperature from 0° C. to 40° C. for 17 to 18 hours to afford the tripeptide (16);

(ii) deprotecting selectively Boc group of tripeptide (16) at a temperature from 0° C. to 40° C. for 30 to 40 minutes by using TFA:DCM (1:1) mixture to obtain free peptide amine (17);

(iii) coupling the free peptide amine (17) at the N-end with Boc-Ala-Ile-OH in the presence of HBTU/HOAt in DMF at a temperature from 0° C. to 40° C. to afford the Boc-protected pentapeptide (18);

(iv) subjecting the Boc-protected pentapeptide (18) to ester saponification at a temperature from 0° C. to 40° C. in water for 4 hours, followed by concurrent Boc-deprotection and O-demethylation by using HBr in AcOH at a temperature from 35° C. to 40° C. for 1 hour to afford deprotected pentapeptide (19).

In yet another embodiment, the present invention provides a novel peptide comprising:

(i) Tripeptide (15):

(15)

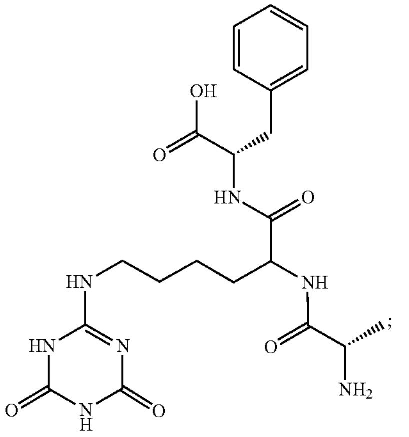

and (ii) Pentapeptide (19);

(19)

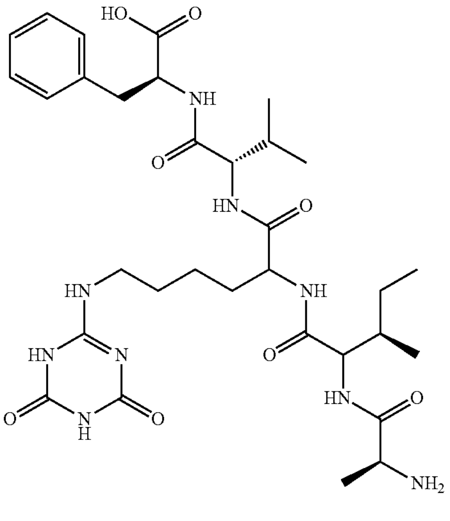

In yet another embodiment, the triple G-C-T nucleobase amino acids of Formula (11) and Formula (9) find wide-ranging application for nucleic acid recognition and nucleic acid-peptide/protein interaction studies.

EXAMPLES

Unless otherwise stated, all chemicals and reagents were obtained commercially. Compound (10) was synthesized as per the reported procedure.

Example 1

General Procedures

Boc-Deprotection of Compounds (12) and (16)

The Boc protected compounds (12) and (16) were subjected to deprotection by using TFA:DCM (1:1) mixture for 30 minutes at 0° C. to 40° C. After completion of reaction, the mixture was stripped off and co-evaporated with toluene: methanol (9:1) at least two times to afford the peptide amines (13) and (17), which were used for next steps without further purification.

Hydrolysis of Esters (14) and (18) to Their Acids

To the solutions of esters (14) and (18) (1 equiv.) in methanol, $LiOH{\cdot}H_2O$ (5 equiv.) was added in water at 0° C. and the reaction mixture was stirred for 4 hours. After the complete consumption of the starting material, the solvent was evaporated under reduced pressure and the residue was treated with sat. $KHSO_4$ solution and was followed by extraction with EtOAc twice. The corresponding acid derivatives, obtained after evaporation of the solvent were taken for the next reaction without further purification.

Demethylation and Boc Deprotection of (11), (14), and (18)

A solution of (11), (14), and (18) (1 equiv.) in 1 mL HBr in AcOH was stirred for 1 hour. Then, diethyl ether ($Et_2O$) was added to the reaction mixture and the resultant solid was washed three times with $Et_2O$ and dried under vacuum giving (9), (15), and (19) respectively, which were hygroscopic.

Scheme 2 Synthesis of G-C-T triple base coded amino acid precursor (11) and its fully deprotected amino acid (9).

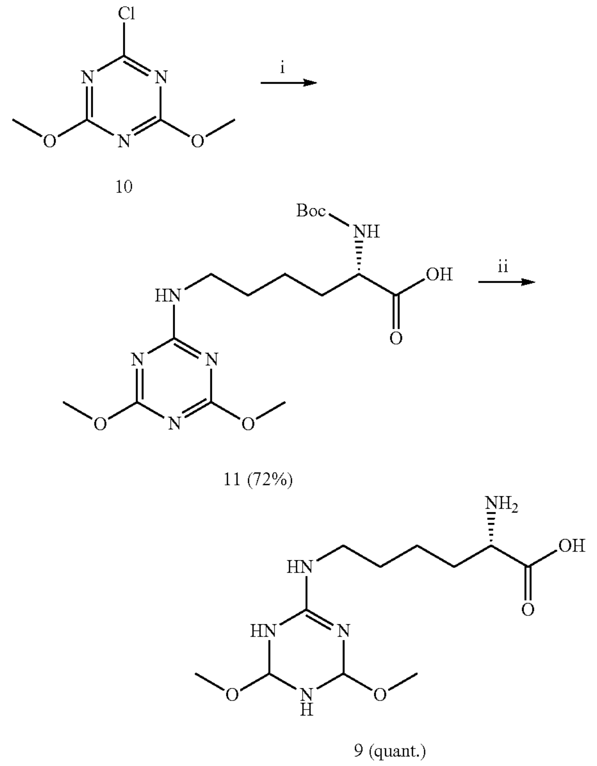

The reaction conditions for Scheme 2 are as follows:

(i) $N_\alpha$-boc-L-lys-OH, DIPEA, MeOH, room temperature (rt), 3 h;

(ii) HBr in AcOH, rt, 1 h.

Figure 3:
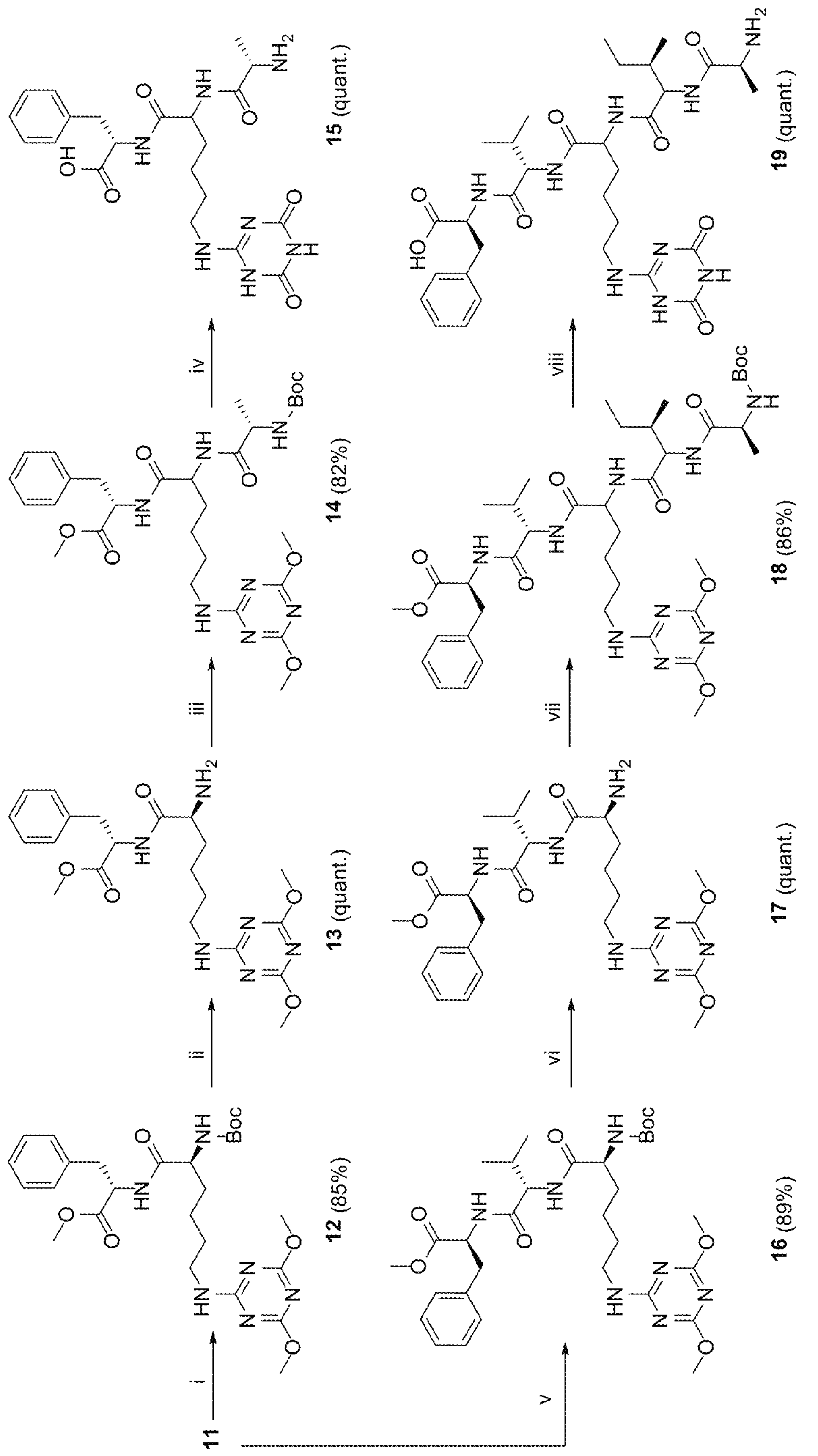
FIG. 3 is a reaction scheme for the synthesis of fully deprotected peptide analogues disclosed herein.

Scheme 3 for the synthesis of fully deprotected peptide analogues (15) and (19) is provided in FIG. 3. The reaction conditions Scheme 3 are as follows:

(i) $NH_2$-Phe-OMe. HCL salt, HBTU, HOAt, DIPEA, DMF, rt, 18 h;

(ii) TFA:DCM (1:1) 0° C. to rt, 0.5 h;

(iii) Boc-Ala-OH, HBTU, HOAt, DIPEA, DMF, rt, 18 h;

(iv) (a) LiOH, MeOH, $H_2O$, rt, 4 hrs; (b) HBr in AcOH, rt, 1 h;

(v) $NH_2$-Val-Phe-OMe, HBTU, HOAt, DIPEA, DMF, rt, 18 h;

(vi) TFA:DCM (1:1) 0° C. to rt, 0.5 h;

(vii) Boc-Ala-Ile-OH, HBTU, HOAt, DIPEA, DMF, rt, 18 h;

(viii) (a) LiOH, MeOH, $H_2O$, rt, 4 hrs; (b) HBr in AcOH, rt, 1 h.

Scheme 3 Synthesis of model compound (20)

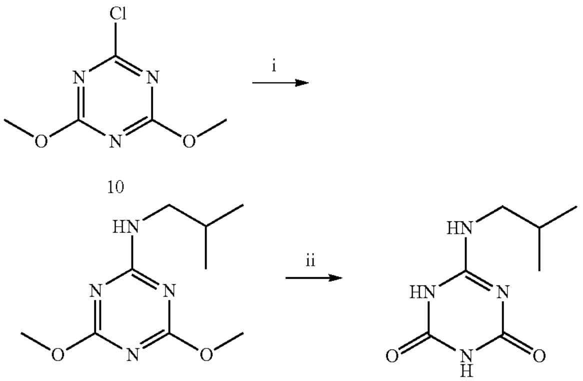

10

20 (quant.)

The reaction conditions for Scheme 3 are as follows:

(i) isobutyl amine, DIPEA, MeOH, rt, 3 h;

(ii) HBr in AcOH, rt, 1 h.

Example 2

Preparation of Compound (11)

(11)

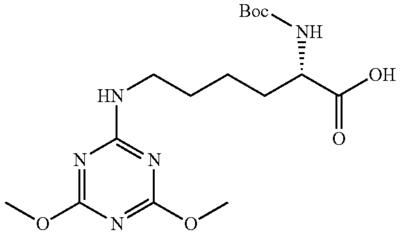

Compound 10 (0.50 g, 2.857 mmol, 1 equiv.) was reacted with $N_\alpha$-boc-L-lys-OH (0.913 g, 3.714 mmol, 1.3 equiv.) in dry methanol (8 mL) as solvent in the presence of N,N-diisopropylethylamine (DIPEA) (0.631 mL, 3.428 mmol, 1.2 equiv.) as a base at 35-40° C. for 2 hrs. After the completion of reaction, methanol was evaporated on rotavapor.

The resulting reaction mixture was dissolved in water, and the water layer was washed with diethyl ether. The aqueous layer further acidified with aq. $KHSO_4$ (pH=3-4), and product was extracted with EtOAc (3x25 mL). The organic layer was dried over $Na_2SO_4$ and concentrated in vacuum to afford the compound 11 (0.790 g, 71%) as a sticky liquid.

$[\alpha]^{25}_{D}$=−1.63° (c=0.2, MeOH); $^1$H NMR (400 MHz, $CDCl_3$) δ: 7.72 (bs, 1H), 5.45-5.43 (d, J=8.01 Hz, 1H), 4.39-4.36 (q, 1H), 3.97 (s, 3H), 3.93 (s, 3H), 3.61-3.57 (m, 1H), 3.29-3.27 (m, 1H), 1.88-1.81 (m, 2H), 1.65-1.54 (m, 2H), 1.44 (s, 9H), 1.44 (s, 1H), 1.28-1.24 (m, 1H); $^{13}$C NMR (100 MHz, $CDCl_3$) δ: 176.5, 173.4, 172.0, 171.1, 166.7, 155.3, 79.7, 55.3, 54.7, 54.7, 53.3, 40.6, 31.9, 28.5, 28.3, 21.8; HRMS (ESI) calculated $[M+H]^+$ for $C_{16}H_{27}N_5O_6$: 385.1961, found 386.2039 $[M+H]^+$.

Example 3

Preparation of Compound (9)

(9)

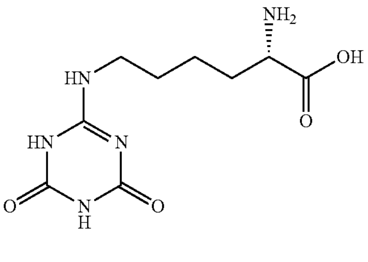

The product (9) was obtained in quantitative yield as a hygroscopic solid using the general procedure for demethylation and Boc deprotection.

$[\alpha]^{25}_{D}$=−0.13° (c=0.2, MeOH); $^1$H NMR (500 MHz, $D_2O$) δ: 4.03-4.0 (t, 1H), 3.38-3.34 (t, 2H), 1.97-1.80 (m, 2H), 1.66-1.59 (m, 2H), 1.51-1.32 (m, 2H); $^{13}$C NMR (125 MHz, $CDCl_3$) δ: 171.8, 152.2, 150.7, 149.2, 52.6, 41.7, 29.2, 27.0, 21.3; HRMS (ESI) calculated $[M+H]^+$ for $C_9H_{16}N_5O_4$: 257.1124, found 258.194 $[M+H]^+$.

Example 4

Preparation of Compound (12)

(12)

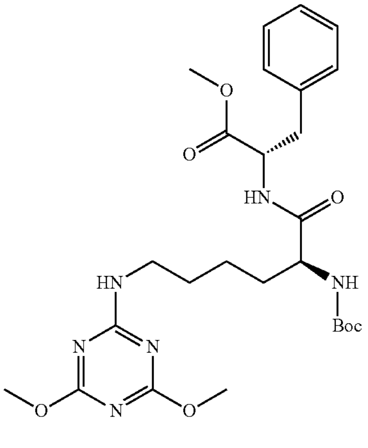

A solution containing acid (11) (0.10 g, 0.259 mmol, 1 equiv.) in dry DMF (2 mL) was cooled at 0° C. To this reaction mixture, HBTU (0.147 g, 0.389 mmol, 1.5 equiv.) was added followed by HOAt (0.028 g, 0.207 mmol, 0.8 equiv.) and DIPEA (0.167 mL, 0.909 mmol, 3.5 equiv.). Finally, L-phenylalanine methyl ester hydrochloride salt (0.072 g, 0.337 mmol, 1.3 equiv.) was added.

The reaction mixture was stirred at 0° C. for 10 minutes and then at 35-40° C. for 18 h. After completion of the reaction, reaction mixture was added into the ice water and extracted with EtOAc twice. The combined EtOAc layer was washed sequentially with sat. $NaHCO_3$, sat. $KHSO_4$, water and brine solution. EtOAc layer was then dried over $Na_2SO_4$, filtered, and concentrated under reduced pressure. Purification by column chromatography (eluent: 50% AcOEt/pet. ether, Rf: 0.5) afforded compound (12) (0.120 g, 85%) as a white solid. mp: 87-89° C.;

$[\alpha]^{25}_{D}$=−8.07° (c=0.2, MeOH); $^{1}H$ NMR (400 MHz, $CDCl_3$) δ: 7.29-7.21 (m, 3H), 7.11-7.09 (m, 2H), 6.58-6.56 (d, J=7.38 Hz, 1H), 5.72 (s, 1H), 5.05-5.03 (d, J=7.13 Hz, 1H), 4.87-4.82 (q, 1H), 4.12-4.06 (m, 1H), 3.94 (s, 3H), 3.90 (s, 3H), 3.71 (s, 3H), 3.42-3.37 (q, 2H), 3.17-3.05 (m, 2H), 1.84-1.75 (m, 1H), 1.64-1.50 (m, 3H), 1.42 (s, 9H), 1.39-1.33 (m, 2H); $^{13}C$ NMR (100 MHz, $CDCl_3$) δ: 172.4, 171.8, 177.7, 177.6, 168.0, 155.4, 135.6, 129.1, 128.5, 127.0, 80.0, 54.5, 54.4, 54.2, 53.0, 52.3, 40.5, 37.7, 32.0, 28.8, 28.2, 22.5; HRMS (ESI) calculated $[M+H]^+$ for $C_{26}H_{39}N_6O_7$: 546.2802, found 547.2883 $[M+H]^+$.

Example 5

Preparation of Compound (14)

(14)

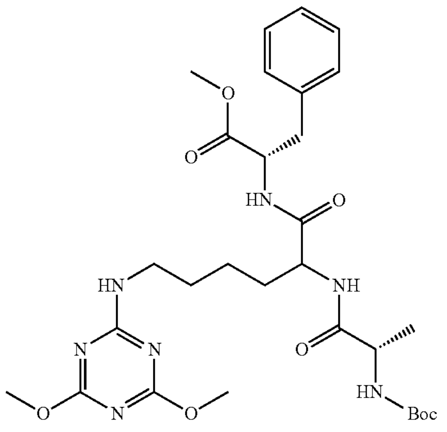

A solution Boc-ala-OH (0.100 g, 0.460 mmol, 1 equiv.) in dry DMF (3 mL) was cooled at 0° C. To the reaction mixture HBTU (0.261 g, 0.691 mmol, 1.5 equiv.), HOAt (0.050 g, 0.368 mmol, 0.8 equiv.) and DIPEA (0.297 mL, 1.612 mmol, 3.5 equiv.) were added. Finally, free amine (13) (0.267 g, 0.599 mmol, 1.3 equiv.) was added.

The reaction mixture was stirred at 0° C. for 10 minutes and at 35-40° C. for 18 h. After completion of the reaction, reaction mixture was added into ice water and extracted with EtOAc twice. The combined EtOAc layer was washed sequentially with sat. $NaHCO_3$, sat. $KHSO_4$, water and brine solution. EtOAc layer was then dried over $Na_2SO_4$, filtered, and concentrated under reduced pressure. Purification was by column chromatography (eluent: 80% AcOEt/pet. ether, Rf: 0.5) afforded (14) (0.245 g, 82%) as a white solid. mp: 143-145° C.

$[\alpha]^{25}_{D}$=−25.01° (c=0.2, MeOH); $^{1}H$ NMR (500 MHz, $CDCl_3$) δ: 7.25-7.17 (m, 3H), 7.11 (bs, 1H), 7.08-7.07 (m, 2H), 6.95 (bs, 1H), 6.32 (bs, 1H), 5.56 (bs, 1H), 4.82-4.78 (q, 1H), 4.45-4.41 (q, 1H), 4.23 (bs, 1H), 3.91 (s, 3H), 3.88 (s, 3H), 3.68 (s, 3H), 3.37-3.33 (q, 2H), 3.12-3.02 (m, 2H),1.81-1.74 (m, 1H), 1.63-1.47 (m, 3H), 1.38 (s, 9H), 1.34-1.27 (m, 6H); $^{13}C$ NMR (125 MHz, $CDCl_3$) δ: 173.1, 172.3, 171.7, 171.1, 167.8, 155.5, 135.7, 129.0, 128.4, 126.9, 79.8, 54.4, 54.3, 53.2, 52.7, 52.2, 49.8, 40.4, 37.5, 31.7, 29.5, 28.4, 28.1, 22.3, 18.0; HRMS (ESI) calculated $[M+H]^+$ for $C_{29}H_{43}N_7O_8$: 617.3173, found 618.3252 $[M+H]^+$.

Example 6

Preparation of Compound (15)

(15)

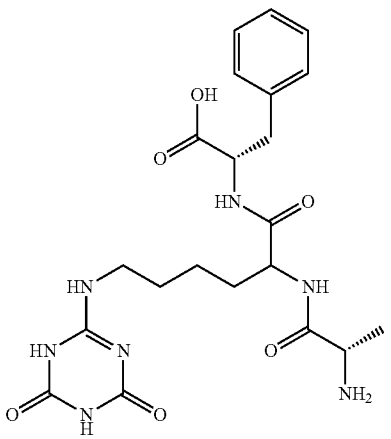

The compound (15) was obtained in quantitative yield as a hygroscopic solid using the general procedure for demethylation and Boc deprotection. $[\alpha]^{25}_{D}$=−0.15° (c=0.2, MeOH); $^{1}H$ NMR (500 MHz, $D_2O$) δ: 7.23-7.21 (m, 2H), 7.17-7.13 (m, 3H), 4.56-4.54 (m, 1H), 4.15-4.13 (t, 1H), 3.99-3.95 (m, 1H), 3.27-3.21 (m, 2H), 3.10-3.07 (m, 1H), 2.94-2.85 (m, 1H), 1.58-1.55 (m, 2H), 1.52-1.49 (m, 2H), 1.34-1.31 (d, 3H), 1.27-1.13 (m, 2H); $^{13}C$ NMR (125 MHz, $D_2O$) δ: 174.3, 173.0, 170.4, 151.9, 150.3, 149.0, 136.3, 129.2, 128.6, 127.0, 53.7, 53.7, 48.8, 41.9, 36.5, 30.6, 27.0, 21.9, 16.6; HRMS (ESI) calculated $[M+H]^+$ for $C_{21}H_{30}N_7O_6$: 475.2179, found 476.2255 $[M+H]^+$.

Example 7

Preparation of Compound (16)

(16)

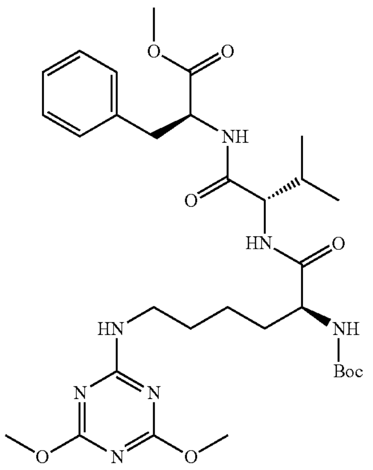

A solution containing acid (11) (0.100 g, 0.259 mmol, 1 equiv.) in dry DMF (2 mL) was cooled at 0° C. To the reaction mixture was added HBTU (0.147 g, 0.389 mmol, 1.5 equiv.) followed by HOAt (0.028 g, 0.207 mmol, 0.8 equiv.) and DIPEA (0.167 mL, 0.909 mmol, 3.5 equiv.). Finally, the dipeptide ($NH_2$-Val-Phe-OMe) (0.072 g, 0.337 mmol, 1.3 equiv.) was added.

The reaction mixture was stirred at 0° C. for 10 minutes and at 35-40° C. for 18 h. After completion of the reaction, reaction mixture was added into the ice water. The resulting solid was filtered and dried under vacuum affording (16) (89%) as a white solid. Note: Before submitting for NMR, compound (16) was washed with $Et_2O$ twice. mp: 150-152° C.;

$[\alpha]^{25}_{D}$=−23.82° (c=0.2, MeOH); $^{1}$H NMR (400 MHz, $CDCl_3$) δ: 7.31-7.22 (m, 3H), 7.11-7.09 (m, 2H), 6.76-6.74 (d, J=8.25 Hz, 1H), 6.57-6.55 (d, J=7.50 Hz, 1H), 5.82 (s, 1H), 5.14-5.12 (d, J=7.88 Hz, 1H), 4.90-4.85 (q, 1H), 4.28-4.24 (m, 1H), 4.08-4.05 (m, 1H), 3.95 (s, 3H), 3.91 (s, 3H), 3.71 (s, 3H), 3.44-3.39 (q, 2H), 3.11-3.09 (m, 2H), 1.87-1.78 (m, 1H), 1.68-1.53 (m, 3H), 1.43 (s, 9H), 1.40-1.37 (m, 2H), 0.92-0.88 (m, 6H); $^{13}$C NMR (100 MHz, $CDCl_3$) δ: 172.4, 172.1, 171.9, 171.7, 170.6, 168.0, 135.6, 129.1, 128.5, 127.1, 80.1, 58.4, 54.5, 54.4, 53.1, 52.3, 40.5, 37.8, 30.7, 29.6, 28.8, 28.2, 22.7, 19.0, 17.7; HRMS (ESI) calculated $[M+H]^+$ for $C_{31}H_{48}N_7O_8$: 645.3486, found 646.3564 $[M+H]^+$.

Example 8

Preparation of Compound (18)

(18)

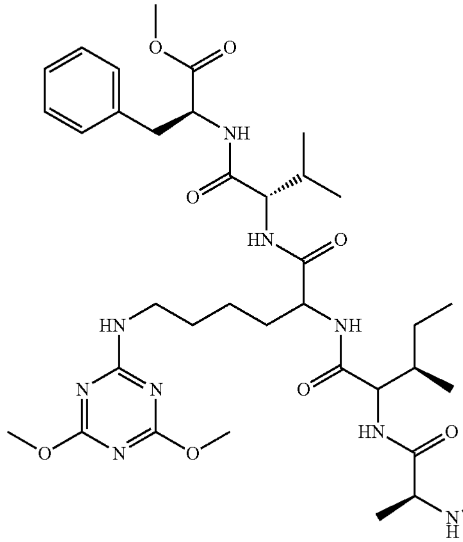

A solution Boc-Ala-Ile-OH (0.050 g, 0.165 mmol, 1 equiv.) in dry DMF (2 mL) was cooled to 0° C. To the reaction was added HBTU (0.094 g, 0.248 mmol, 1.5 equiv.) followed by HOAt (0.018 g, 0.132 mmol, 0.8 equiv.) and DIPEA (0.106 mL, 0.579 mmol, 3.5 equiv.). Finally, free amine (17) (0.117 g, 0.215 mmol, 1.3 equiv.) was added.

The reaction mixture was stirred at 0° C. for 10 minutes and at 35-40° C. for 18 h. After completion of the reaction, reaction mixture was added into ice water. The resulting solid was filtered and dried under vacuum affording (10) (85%) as a white solid. Note: Before submitting for NMR, compound 18 was washed with $Et_2O$ twice. mp: 226-228° C.;

$[\alpha]^{25}_{D}$=143.44° (c=0.2, MeOH); $^{1}$H NMR (400 MHz, DMSo-$d_6$) δ: 8.40-8.37 (t, $1H)_{rotamer}$, 8.06-7.98 (m, $1H)_{rota}$, 7.87-7.84 (m, $1H)_{rotamer}$, 7.72-7.65 (dd, $1H)_{rotamer}$, 7.60-7.55 (dd, $1H)_{rotamer}$, 7.26-7.23 (m, 2H), 7.20-7.17 (m, 3H), 7.04-6.94 (dd, $1H)_{rotamer}$, 4.49-4.44 (m, $1H)_{rotamer}$, 4.37-4.35 (m, $1H)_{rotamer}$, 4.28-4.24 (m, $1H)_{rotamer}$, 4.21-4.14 (m, $1H)_{rotamer}$, 4.04-3.93 (m, $1H)_{rotamer}$, 3.80 (s, 3H), 3.79 (s, 3H), 3.55 (s, 3H), 3.24-3.18 (m, $2H)_{rotamer}$, 3.03-2.99 (m, $2H)_{rotamer}$, 2.94-2.89 (m, $1H)_{rotamer}$, 1.93-1.85 (m, $1H)_{rotamer}$, 1.75-1.67 (m, $1H)_{rotamer}$, 1.57-1.55 (m, $1H)_{rotamer}$, 1.48-1.42 (m, $3H)_{rotamer}$, 1.36 (s, 9H), 1.27-1.21 (m, $3H)_{rotamer}$, 1.16-1.13 (t, $3H)_{rotamer}$, 1.07-1.01 (m, $1H)_{rotamer}$, 0.82-0.72 (m, $12H)_{rotamer}$; $^{13}$C NMR (100 MHz, $CDCl_3$) δ: 172.7, 172.5, 172.0, 171.7, 171.5, 171.4, 171.2, 171.0, 171.0, 171.0, 170.9, 170.7, 167.6, 167.5, 155.1, 155.0, 137.0, 128.9, 128.9, 128.2, 126.5, 79.1, 78.1, 57.2, 57.1, 56.5, 55.2, 54.0, 54.0, 53.9, 53.4, 52.5, 52.3, 51.7, 50.1, 49.8, 37.3, 37.0, 36.5, 31.6, 31.3, 30.9, 30.7, 28.4, 28.1, 25.7, 24.0, 22.7, 22.7, 19.0, 18.9, 18.2, 17.9, 17.9, 17.8, 15.2, 14.1, 11.4, 11.0; HRMS (ESI) calculated $[M+H]^+$ for $C_{40}H_{63}N_9O_{10}$: 829.4698, found 830.4776 $[M+H]^+$.

Example 9

Preparation of Compound (19)

(19)

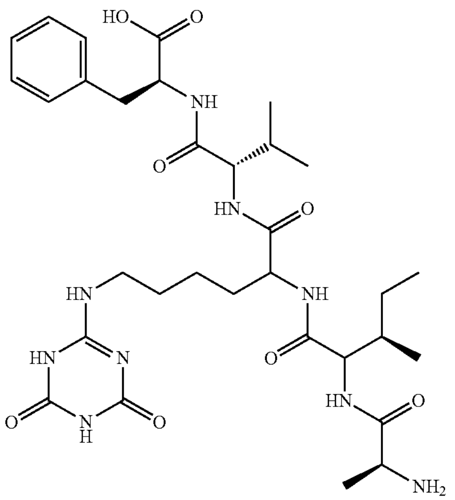

The product (19) was obtained in quantitative yield as a hygroscopic solid using the general procedure for demethylation and Boc deprotection. $[\alpha]^{25}{}_{D}$=−0.19° (c=0.2, MeOH); $^{1}$H NMR (400 MHz, $CDCl_3$) δ: 7.26-7.21 (m, 3H), 7.17-7.15 (m, 2H), 4.62-4.58 (m, 2H), 4.27-4.21 (m, 2H), 4.13-4.00 (m, 3H), 3.36-3.11 (m, 1H), 2.98-2.92 (m, 1H), 1.95-1.81 (m, 2H), 1.79-1.71 (m, 1H), 1.66-1.63 (m, 2H), 1.61-1.54 (m, 2H), 1.49-1.44 (m, 4H), 1.33-1.20 (m, 3H), 1-18-1.09 (m, 1H), 0.84-0.78 (m, 12H); $^{13}$C NMR (100 MHz, $CDCl_3$) δ: 174.2, 173.3, 173.1, 172.8, 172.7, 171.1, 170.6, 151.3, 149.2, 149.1, 148.4, 136.4, 129.1, 128.6, 127.0, 59.1, 58.3, 57.6, 53.8, 53.5, 53.2, 49.1, 48.8, 42.2, 36.5, 36.3, 36.1, 30.5, 30.4, 30.3, 30.1, 26.9, 25.5, 24.5, 22.2, 22.0, 18.2, 17.8, 17.7, 16.8, 16.7, 14.6, 14.0, 10.6, 10.2; HRMS (ESI) calculated $[M+H]^+$ for $C_{32}H_{50}N_9O_8$: 687.3704, found 688.3778 $[M+H]^+$.

Example 10

Preparation of Compound (20)

(20)

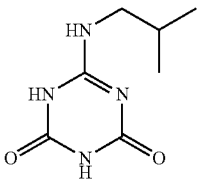

The intermediate N-isobutyl-4,6-dimethoxy-1,3,5-triazin-2-amine was synthesized by using the same procedure for compound (11) by using isobutyl amine. Finally, the compound was obtained in quantitative yield as a white solid using the general procedure for demethylation and Boc deprotection. $^{1}$H NMR (400 MHz, DMSO-$d_6$) δ: 11.65 (bs, 1H), 11.15 (s, 1H), 8.73 (bs, 1H), 3.17-3.16 (d, J=6.87 Hz, 2H), 1.85-1.77 (bs, 1H), 0.88-0.87 (d, J=6.87 Hz, 6H); $^{13}$C NMR (100 MHz, DMSO-$d_6$) δ: 152.7, 150.1, 150.0, 148.1, 48.2, 27.6, 19.6.

Example 11

X-Ray Crystal Structure Analysis of Compound (20)

About 0.1 g of 20 was dissolved in 1.5 mL of dimethylformamide. This solution was kept at 35-40° C. for 4 days and afforded needle-shaped colorless crystals.

Single-crystal data of compound 20 was collected on a Bruker SMART APEX four-circle diffractometer equipped with a CMOS photon 100 detector (Bruker Systems Inc.) and with a Cu Kα radiation (1.5418 Å). The incident X-ray was focused and monochromated using Micro focus (IμS). Crystal of compound 20 was mounted on nylon Cryo loops with Paratone-N oil. Full data was collected at 100 K maintained by "Cryoconnector" and liquid nitrogen. Data was integrated using Bruker SAINT software and was corrected for absorption using SADABS. Structure was solved by Intrinsic Phasing method and refined using the SHELXTL 2017 software suite. All non-hydrogen atoms were located from iterative examination of difference F-maps, following which, the structure was refined using a least-squares method. Hydrogen atoms were placed geometrically and placed in a riding model. The parameters are given in TABLE 1 below.

TABLE 1

| Parameters | Compound 12 | |
|---|---|---|
| Chemical formula | $C_7H_{12}N_4O_2$ | |
| Formula weight | 184.19 | |
| Crystal system | Triclinic | |
| Space group | P-1 | |
| Unit-cell parameters | a = 9.132 (7) Å | α = 76.88 (8)° |
| | b = 9.455 (11) Å | β = 89.63(7)° |
| | c = 14.002(15) Å | γ = 71.51(6)° |
| Crystal color and shape | Colorless-needle | |
| Temperature | 100K | |
| No. of formula units in the unit cell (Z) | 2 | |
| Density (g $cm^{-1}$) | 1.32 | |
| Abs. Coeff. ($mm^{-1}$) | 0.831 | |
| F(000) | 472 | |
| Reflection data | | |
| No. of reflections meas. | 19754 | |
| No. of unique reflections | 3963 | |
| No. of obs. reflections | 2737 | |
| λ (Å) | 1.54178 | |
| $R_{merge}$ | 0.092 | |
| Av. I/sig(1) | 14.90 | |
| Index ranges | −10 ≤ h ≤ 9, −11 ≤ k ≤ 11, −16 ≤ l ≤ 16 | |
| $\theta_{max}$ | 68.7 | |
| $\theta_{min}$ | 5.1 | |
| Refinement Data | | |
| Absorption correction type | multi-scan | |
| $T_{min}$ | 0.638 | |
| $T_{max}$ | 0.779 | |
| $R_{all}$ | 0.126 | |
| $R_{obs}$ | 0.092 | |
| $wR_2$(all) | 0.281 | |
| $wR_2$(obs) | 0.259 | |
| Goodness-of-fit (GOOF) | 1.070 | |
| Largest diff. peak and hole: Delta-rho ($eÅ^{-3}$)$_{max}$ | 0.524 | |

TABLE 1-continued

| Parameters | Compound 12 |
|---|---|
| Largest diff. peak and hole: Delta-rho (e$Å^{-3}$)$_{min}$ | −0.369 |

Thus, the present disclosure provides a triple G-C-T nucleobase amino acid (G-C-TNBA), featuring three recognition faces: DDA (G mimic), DAA (C mimic) and ADA (T mimic). The G-C-TNBA is readily obtainable in multi-gram scale in a remarkably facile one-step reaction.

Owing to the prototropy effect, the triple G-C-T base can exist in two forms, displaying G and T faces and C and T faces. This suggests that it can simultaneously interact with two sets of nucleobases (C-A or G-A) at any given time.

We claim:

1. A triple G-C-T base coded nucleobase amino acid, comprising a compound according to formula (I):

(I)

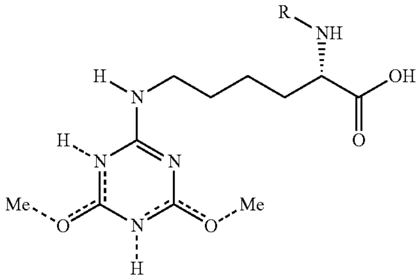

where R is —H or -Boc, wherein:

the triple G-C-T base coded nucleobase amino acid comprises three recognition sites that can simultaneously interact with two sets of nucleobases at any given time;

the three recognition sites comprise DDA as a G mimic, DAA as a C mimic, and ADA as a T mimic; and the two sets of nucleobases comprise C-A and G-A.

2. The triple G-C-T base coded nucleobase amino acid of claim 1, wherein the compound according to formula (I) is compound (9) or compound (11):

(9)

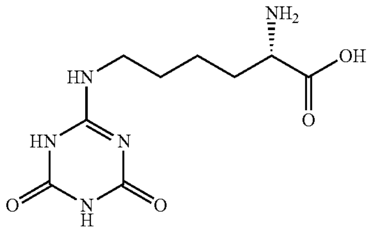

(11)

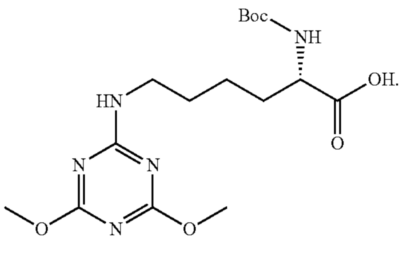

3. The triple G-C-T base coded nucleobase amino acid of claim 2, wherein the compound according to formula (I) is compound (9).

4. The triple G-C-T base coded nucleobase amino acid of claim 2, wherein the compound according to formula (I) is compound (11).

5. A method for preparing the triple G-C-T base coded nucleobase amino acid according to claim 1, wherein the compound according to formula (I) is compound (9):

(9)

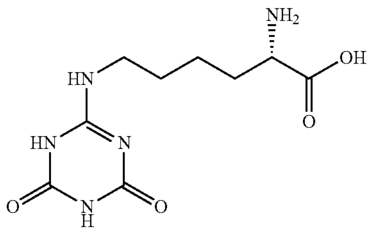

the method comprising:

(a) reacting 2-chloro-4,6-dimethoxy-1,3,5-triazine (10):

(10)

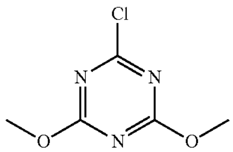

with α-Boc lysine in the presence of base and solvent at a temperature from 35° C. to 40° C. for 1 hour to 2 hours to obtain a Boc-protected G-C-T-amino acid intermediate (11):

(11)

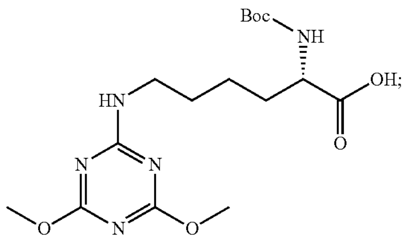

and (b) deprotecting the Boc-protected G-C-T-amino acid intermediate (11) with HBr/AcOH at a temperature from 35° C. to 40° C. for 1 hour to remove a Boc group and demethylate, to obtain, in quantitative yield, free triple G-C-T amino acid compound (9).

6. The method according to claim 5, wherein the base is N,N-diisopropylethyl amine and the solvent is dry methanol.

7. A method for preparing the triple G-C-T base coded nucleobase amino acid according to claim 1, wherein the compound according to formula (I) is compound (11):

(11)

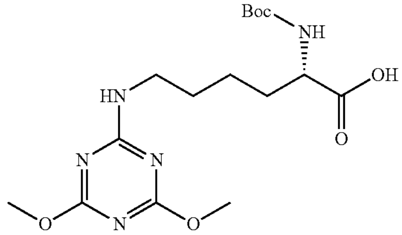

the method comprising:

reacting 2-chloro-4,6-dimethoxy-1,3,5-triazine (10):

(10)

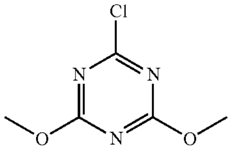

with α-Boc lysine in the presence of base and solvent at a temperature from 35° C. to 40° C. for 1 hour to 2 hours to obtain the compound (11).

8. The method according to claim 7, wherein the base is N,N-diisopropylethyl amine and the solvent is dry methanol.

9. A peptide synthesized from the triple G-C-T base coded nucleobase amino acid according to claim 1 as a nucleobase amino acid building block intermediate, wherein the compound according to formula (I) is compound (11):

(11)

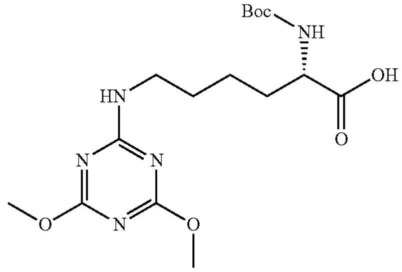

the peptide being chosen from:

a tripeptide compound (15):

(15)

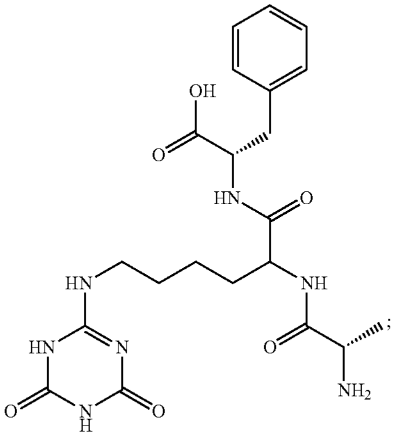

or a pentapeptide compound (19):

(19)

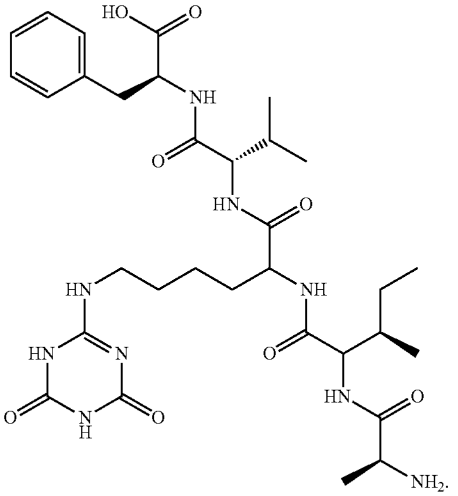

10. A method for synthesizing the peptide according to claim 9, the method comprising:

coupling C-termini of compound (11) with an alpha-amino acid in the presence of HBTU/HOAt in DMF at a temperature from 0° C. to 40° C. for 17 to 18 hours to obtain a peptide;

deprotecting a Boc group at a temperature from 0° C. to 40° C. for 30 to 40 minutes with a TFA:DCM (1:1) mixture to obtain a free peptide amine;

coupling the free peptide amine at an N-terminus further with Boc-protected alpha amino acid in the presence of HBTU/HOAt in DMF at a temperature from 0° C. to 40° C. for 17 to 18 hours to obtain a Boc-protected peptide sequence; and saponifying, deprotecting, and O-demethylating the Boc-protected peptide sequence to obtain the tripeptide compound (15) or the pentapeptide compound (19).

* * * * *